(12) United States Patent
Hara et al.

(10) Patent No.: US 11,238,584 B2
(45) Date of Patent: Feb. 1, 2022

(54) DEVICE, METHOD, AND PROGRAM FOR VISUALIZING NETWORK OF BLOOD VESSELS OF SKIN

(71) Applicants: SHISEIDO COMPANY, LTD., Tokyo (JP); UNIVERSITY PUBLIC CORPORATION OSAKA, Osaka (JP)

(72) Inventors: Yusuke Hara, Kanagawa (JP); Toyonobu Yamashita, Kanagawa (JP); Masato Ninomiya, Kanagawa (JP); Souichi Saeki, Osaka (JP)

(73) Assignees: Shiseido Company, Ltd., Tokyo (JP); University Public Corporation Osaka, Osaka (JP)

( * ) Notice: Subject to any disclaimer, the term of this patent is extended or adjusted under 35 U.S.C. 154(b) by 124 days.

(21) Appl. No.: 16/830,619

(22) Filed: Mar. 26, 2020

(65) Prior Publication Data

US 2020/0226756 A1 Jul. 16, 2020

Related U.S. Application Data

(63) Continuation of application No. PCT/JP2018/024516, filed on Jun. 28, 2018.

(30) Foreign Application Priority Data

Sep. 29, 2017 (JP) .............................. JP2017-189269

(51) Int. Cl.
*G06T 7/00* (2017.01)
*G06T 7/62* (2017.01)
(Continued)

(52) U.S. Cl.
CPC .......... *G06T 7/0012* (2013.01); *A61B 5/0066* (2013.01); *A61B 5/489* (2013.01); (Continued)

(58) Field of Classification Search
None
See application file for complete search history.

(56) References Cited

U.S. PATENT DOCUMENTS

2006/0264719 A1 11/2006 Schurman et al.
2015/0374228 A1 12/2015 Satake et al.
(Continued)

FOREIGN PATENT DOCUMENTS

JP 2008537903 A 10/2008
JP 2016010656 A 1/2016
(Continued)

OTHER PUBLICATIONS

Gong, Peijun et al., "Assessment of human burn scars with optical coherence tomography by imaging the attenuation coefficient of tissue after vascular masking", Journal of Biomedical Optics, vol. 19, Nov. 5, 2013, pp. 1-10.

(Continued)

*Primary Examiner* — Vu Le
*Assistant Examiner* — Courtney Joan Nelson
(74) *Attorney, Agent, or Firm* — Muncy, Geissler, Olds & Lowe, P.C.

(57) ABSTRACT

A device of an embodiment includes: an optical mechanism that guides light from a light source to skin tissue to scan the skin tissue; a control computation unit that controls driving of the optical mechanism, acquires tomographic images of the skin by processing optical interference signals from the optical system, and calculates a network of blood vessels on (Continued)

the basis of the tomographic images; and a display device that displays the network of blood vessels. The control computation unit computes autocorrelation values at coordinates in epidermis corresponding regions of the tomographic images, excludes combinations of tomographic images with the computed autocorrelation values corresponding to predetermined low autocorrelation, computes autocorrelation values at coordinates in dermis corresponding regions, determines coordinates at which the autocorrelation values in the dermis corresponding regions are within a predetermined low correlation range to be blood vessels or blood vessel candidates, and calculates a network of blood vessels.

10 Claims, 14 Drawing Sheets

(51) Int. Cl.
  *G06T 7/66* (2017.01)
  *A61B 5/00* (2006.01)
  *G06T 11/00* (2006.01)

(52) U.S. Cl.
  CPC ............ *A61B 5/7246* (2013.01); *A61B 5/742* (2013.01); *G06T 7/62* (2017.01); *G06T 7/66* (2017.01); *G06T 11/008* (2013.01); *A61B 2576/00* (2013.01); *G06T 2207/10101* (2013.01); *G06T 2207/30088* (2013.01); *G06T 2207/30104* (2013.01); *G06T 2210/41* (2013.01)

(56) References Cited

U.S. PATENT DOCUMENTS

| 2016/0000368 A1 | 1/2016 | Wang et al. |
| 2016/0317027 A1 | 11/2016 | Goto |
| 2018/0279874 A1 | 10/2018 | Yoshida et al. |
| 2019/0125247 A1 | 5/2019 | Saeki et al. |

FOREIGN PATENT DOCUMENTS

| JP | 2016116595 A | 6/2016 |
| JP | 2016209201 A | 12/2016 |
| JP | 2017225811 A | 12/2017 |
| WO | WO2016135454 A1 | 9/2016 |

OTHER PUBLICATIONS

Liu, Xuan et al., Motion analysis and removal in intensity variation based OCT angiography, Biomedical Optics Express, Oct. 7, 2014, vol. 5, pp. 3833-3847.

Chen. C. et al., Removing noises caused by motion artefacts in microcirculation maps of human skin in vivo, Journal of Microscopy, Sep. 10, 2015, vol. 260, pp. 389-399.

Shi, Weisong et al., Differential standard deviation of log-scale intensity based optical coherence tomography angiography, Journal of Biophotonics, Jan. 31, 2017, vol. 10, pp. 1597-1606.

Joey Enfield et al, "In vivo imaging of the microcirculation of the volar forearm using correlation mapping optical coherence tomography (cmOCT)": vol. 2, No. 5; Biomedical Optics Express; May 1, 2011 ; pp. 1184-1193.

David Wei et al, "Automatic motion correction for in vivo human skin optical coherence tomography angiography through combined rigid and nonrigid registration"; Journal of Biomedical Optics 22(6), Jun. 2017; pp. 066013 1-066013-2.

— G

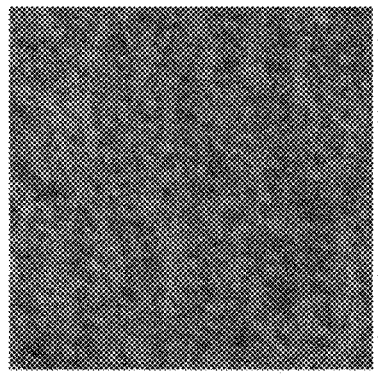
FIG.7A
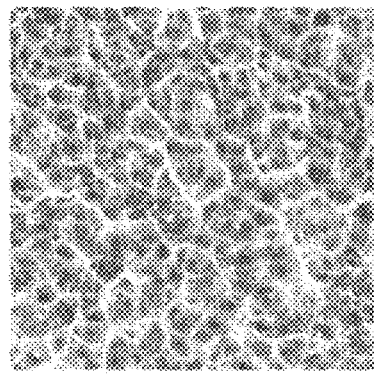
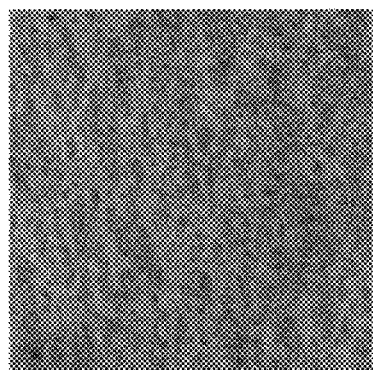
FIG.7B
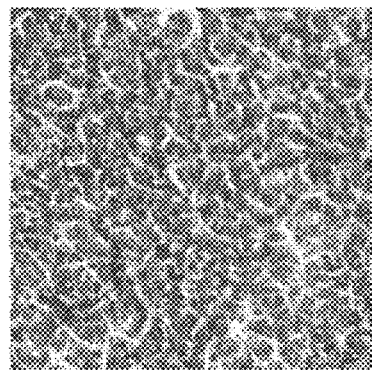
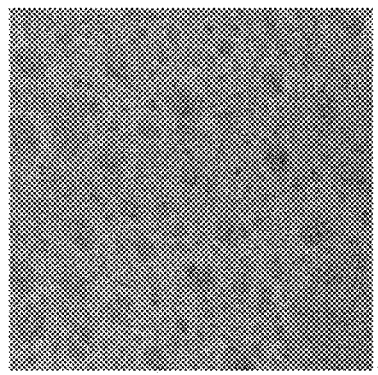
FIG.7C
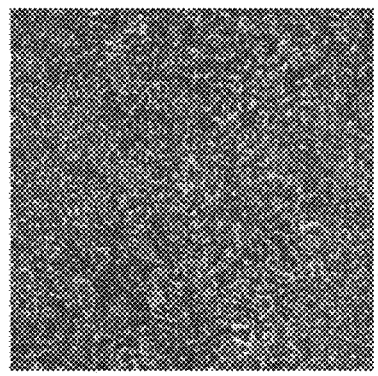
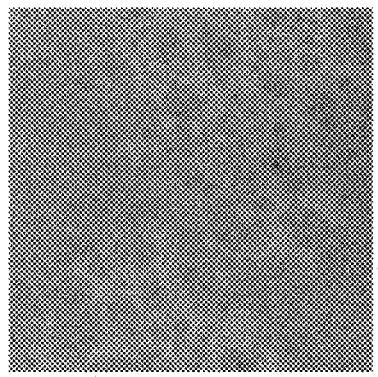
FIG.7D
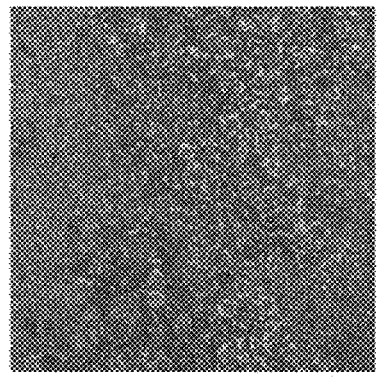

FIG.8B (Thin)

(Thick)
(Thin)

DEVICE, METHOD, AND PROGRAM FOR VISUALIZING NETWORK OF BLOOD VESSELS OF SKIN

CROSS-REFERENCE TO RELATED APPLICATIONS

This application is a continuation application of International Application No. PCT/JP2018/024516, filed on Jun. 28, 2018, which claims priority to and the benefit of Japanese Patent Application No. 2017-189269, filed on Sep. 29, 2017. The contents of these applications are incorporated herein by reference in their entirety.

BACKGROUND OF INVENTION

1. Field

The present invention relates to a device and a method for visualizing a network of blood vessels of skin by using optical coherence tomography (OCT).

2. Description of Related Art

Skin serves such important roles as preventing loss of moisture, themoregulating through heat exchange with external environment, protecting a living body from physical irritation, and perceiving senses such as touch. Skin tissue is mainly constituted by three layers, which are epidermis, dermis, and subcutaneous tissue. Capillaries run in and under dermis, and supply oxygen and nutrients to skin cells to provide firmness and moisture to the skin. Reduction in the elasticity of capillaries due to aging and environmental changes such as ultraviolet rays is considered as a cause of symptoms of aging of the skin such as winkles and sagging. Thus, technologies of visualizing a network of blood vessels of skin for evaluation of effective skin care are drawing attention.

A method using the OCT has been proposed as such a technology for visualizing a network of blood vessels (refer to Non-patent Literature 1, for example). The OCT is tomography using low-coherence optical interference, which enables visualization of distribution of biological tissue forms at high spatial resolution in microscale. The OCT is also advantageous in achieving an image acquisition rate not lower than the video rate, and high temporal resolution.

RELATED ART LIST

Non-patent Literature 1: J. Enfield, E. Jonathan, M. Leahy, In vivo imaging of the microcirculation of the volar forearm using correlation mapping optical coherence tomography (cmOCT), Biomed. Opt. Express 2 (2011) 1184-1193

Non-patent Literature 2: D Wei et al., "Automatic motion correction for in vivo human skin OCT angiography through combined rigid and nonrigid registration," J Biomed Opt, 22(6), 066013 (2017)

During such OCT measurement, however, a minute motion of a blood flow is likely to be contaminated with noise due to body motion, and it is thus not easy to acquire a clear image of a network of blood vessels. Although various filters have been proposed for removal of such noise (refer to Non-patent Literature 2, for example), these are disadvantageous in complicated arithmetic processing, which increases the cost.

SUMMARY OF INVENTION

In view of the above and other circumstances, one of objects of the present invention is to realize visualization of a network of blood vessels of skin using the OCT with high accuracy by a simple technique.

An embodiment of the present invention relates to a blood vessel visualizing device that includes an optical system using the OCT, and visualizes a network of blood vessels of skin. The device includes: an optical mechanism that guides light from a light source to tissue of the skin to scan the skin tissue; a control computation unit that controls driving of the optical mechanism, acquires tomographic images of the skin by processing optical interference signals from the optical system, and calculates a network of blood vessels on the basis of the tomographic images; and a display unit that displays an image of the network of blood vessels. The control computation unit computes autocorrelation values at coordinates in epidermis corresponding regions of a plurality of acquired topographic images of each skin site, excludes combinations of tomographic images with the computed autocorrelation values corresponding to predetermined low autocorrelation, then computes autocorrelation values at coordinates in dermis corresponding regions, and determines, as blood vessels or blood vessel candidates, coordinates at which the autocorrelation values in the dermis corresponding regions are within a predetermined low correlation range, and calculates the network of blood vessels.

Another embodiment of the present invention relates to a blood vessel visualizing method for visualizing a network of blood vessels of skin. The method includes: a tomographic image acquiring step of acquiring tomographic images of the skin by using optical coherence tomography; a computation specifying step of determining tomographic images in which influence of noise due to body motion exceeds a reference value among the acquired tomographic images, and excluding the determined tomographic images from computation; a computing step of calculating a network of blood vessels on the basis of tomographic images subject to computation; and a displaying step of displaying the calculated network of blood vessels.

The present invention achieves visualization of a network of blood vessels of skin with high accuracy by a simple technique.

BRIEF DESCRIPTION OF DRAWINGS

FIGS. 7A to 7D show results of calculation of a network of blood vessels;

FIGS. 8A to 8C show a blood vessel thickness displaying process;

DETAILED DESCRIPTION

Figure 1:
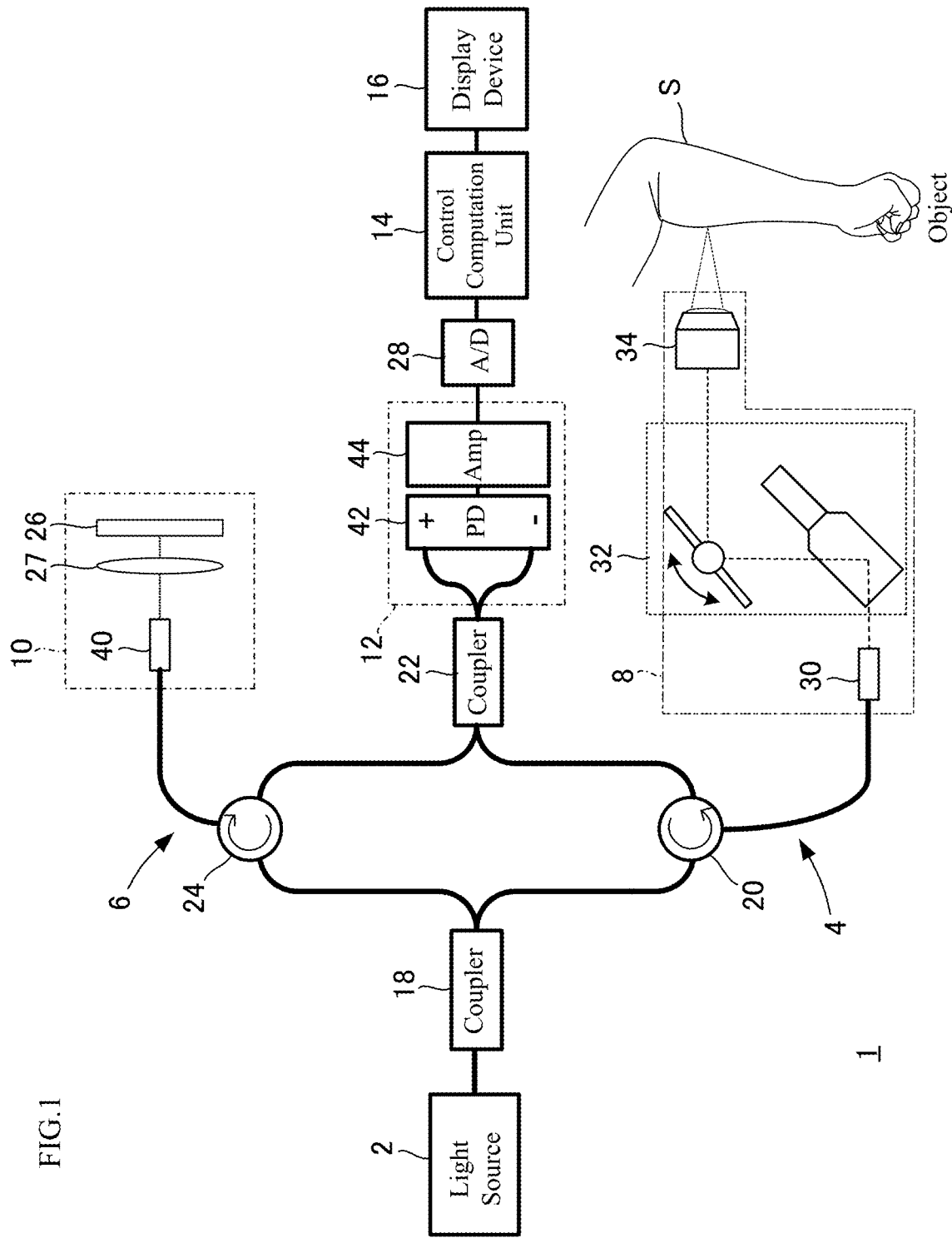
FIG. 1 is a diagram schematically illustrating a configuration of a blood vessel visualizing device according to an example.

One embodiment of the present invention is a blood vessel visualizing device. The device includes an optical mechanism and a control computation unit. The control computation unit controls driving of the optical mechanism, and acquires tomographic images of skin by using the OCT. The control computation unit calculates the shape (two-dimensional shape or three dimensional shape) of a network of blood vessels on the basis of the tomographic images, and displays the mages on a display unit. The device is capable of reducing body motion noise, extracting blood vessel sites with high accuracy, and visualizing the thicknesses of blood vessels in display processing of a network of blood vessels.

(1) Reduction of Body Motion Noise

In the present embodiment, an OCT image of each skin site from the epidermis to the dermis thereof is acquired a plurality of times (a plurality of times per one cross section). The control computation unit determines, among the acquired tomographic images, tomographic images in which the influence of body motion noise exceeds a reference value. The control computation unit then excludes the determined tomographic images from computation, and calculates a network of blood vessels on the basis of the remaining tomographic images. In this manner, an image of a network of blood vessels with reduced body motion noise can be displayed.

Specifically, before calculating a network of blood vessels on the basis of autocorrelation of tomographic images according to a technique of the related art, a process of sorting out combinations of tomographic images to be used in the autocorrelation is performed. This is to narrow down the computation to the combinations of tomographic images with little body motion noise by using the difference in the sensitivity of the epidermis to blood flows and to body motion. Specifically, no blood vessels are present in the epidermis while blood vessels are present in the dermis. Thus, the dermis has high sensitivity to the motion of blood vessels (that is, blood flow) and likely to be displaced or deformed by the blood flow. In contrast, because the epidermis is spaced from the blood vessels, the epidermis has low sensitivity to the blood flow, but has high sensitivity to body motion. When the displacement of the epidermis is large, it can therefore be assumed that the displacement is caused by body motion. On the basis of this idea, combinations of tomographic images in which the displacement of the epidermis is larger than a criterion are removed from the computation of autocorrelation.

The control computation unit sets an epidermis corresponding region and a dermis corresponding region in a cross-sectional region of skin. Note that an "epidermis corresponding region" may be part of an epidermis region, and may be a region in which a displacement caused by a blood flow is relatively small while a displacement caused by body motion is relatively large. A "dermis corresponding region" may be part of a dermis region, and may be a region in which a displacement caused by a blood flow is relatively large. More specifically, a reticular layer of the dermis belongs to a dermis corresponding region because the blood vessels therein have relatively large diameters and a displacement thereof caused by a blood flow is large. A papillary layer of the dermis need not be included in a dermis corresponding region because the blood vessels therein have relatively small diameters and a displacement thereof caused by a blood flow is small. "Coordinates", which may be spatial coordinates set in the OCT, define positions (cross-sectional positions) of pixels constituting a tomographic image.

The control computation unit may define an epidermis corresponding region and a dermis corresponding region on the basis of an intensity profile in the depth direction of an acquired tomographic image. An "intensity profile" may show OCT intensity (light intensity).

The control computation unit computes autocorrelation values at coordinates in epidermis corresponding regions in a plurality of acquired tomographic images of a skin site (first correlation acquiring process). Subsequently, combinations of tomographic images with the computed autocorrelation values corresponding to predetermined low autocorrelation are excluded from subsequent computation (computation specifying process). This computation specifying process (that is, the process of excluding combinations of tomographic images in which the epidermis corresponding regions have low autocorrelation) reduces contamination with body motion noise.

The control computation unit computes autocorrelation values of coordinates in dermis corresponding regions in the tomographic images remaining after the excluding process (second correlation acquiring process). The control computation unit then determines, as blood vessels or blood vessel candidates, coordinates in the dermis corresponding regions having autocorrelation values present within a predetermined low correlation range, to calculate a network of blood vessels. Specifically, the thus calculated coordinates (pixels corresponding to the coordinates) may be determined as blood vessels, and a network of blood vessels may be calculated as a connection of such coordinates. Alternatively, the thus calculated coordinates may just be determined as blood vessel candidates, and may further be determined as blood vessels depending on an additional condition. The "low correlation range" can be set to a proper range through experiments, analysis, or the like.

According to the present embodiment, visualization of a network of blood vessels is achieved with high accuracy by a simple technique of removing tomographic images with much body motion noise from computation among a plurality of acquired tomographic images of each skin site.

In addition, a blood vessel visualization program using the above-described technology may be built. The program causes a computer to implement a function of computing first autocorrelation values, which are autocorrelation values in epidermis corresponding regions, of a plurality of tomographic images of each skin site acquired by the OCT, a function of excluding combinations of tomographic images with the first autocorrelation values corresponding to predetermined low autocorrelation and then computing second autocorrelation values, which are autocorrelation values in dermis corresponding regions, a function of calculating a network of blood vessels on the basis of the second autocorrelation values, and a function of outputting signals to display the calculated network of blood vessels. The program may be recorded on a computer-readable recording medium.

(2) Accurate Extraction of Blood Vessel Sites

For calculation of a network of blood vessels of skin by the OCT, a blood vessel may be determined on the basis of the OCT intensity (light intensity, or intensity). This is based on blood vessels' property of having lower OCT intensities than surrounding tissue. Sites with low OCT intensities may, however, include lymphatic vessels. In the present embodiment, blood vessels and lymphatic vessels are distinguished from each other on the basis of a preset threshold of OCT intensity, which enables extraction of blood vessel sites with high accuracy.

The control computation unit sets a reference profile obtained by function approximation of an intensity profile in the depth direction of an acquired tomographic image. An "intensity profile" may show the OCT intensity. A tomographic image may be acquired once or may be acquired a plurality of times as described above. In the latter case, an average of OCT intensities in a plurality of images may be obtained. For the "function approximation", linear fitting such as the least-squares method may be employed. For computation of a network of blood vessels focusing on dermis corresponding regions, the setting on the reference profile may be limited to the dermis corresponding regions.

Regarding an intensity value in the depth direction of a tomographic image, the control computation unit calculates a difference between an intensity value on the reference profile and an actual intensity value as an outlier (outlier level). The "intensity value on the reference profile" refers to the intensity (also referred to as "reference intensity") of surrounding tissue other than blood vessels and lymphatic vessels. The intensities of blood vessels and lymphatic vessels are significantly lower than the reference intensity. Thus, a site can be determined not to be surrounding tissue, that is, determined to be a blood vessel or a lymphatic vessel on the basis of calculation of the magnitude of the "outlier", which is the difference between an actually detected intensity and the reference intensity.

The control computation unit determines coordinates having the outliers within a preset blood vessel determination range (a range from a first threshold to a second threshold) to be blood vessels or blood vessel candidates, to calculate a network of blood vessels. Specifically, the thus calculated coordinates (pixels corresponding to the coordinates) may be determined as blood vessels, and a network of blood vessels may be calculated as a connection of such coordinates. Alternatively, the thus calculated coordinates may just be determined as blood vessel candidates, and may further be determined as blood vessels depending on an additional condition. The "blood vessel determination range" can be set to a proper range as a range substantially excluding lymphatic vessels and tissue surrounding blood vessels by experiments, analysis, or the like.

The control computation unit may determine coordinates having the outliers within a lymphatic vessel determination range (a range exceeding the second threshold), which is set to a lower intensity range than the blood vessel determination range, to be lymphatic vessels or lymphatic vessel candidates. Specifically, the thus calculated coordinates (pixels corresponding to the coordinates) may be determined as lymphatic vessels. Alternatively, the thus calculated coordinates may just be determined as lymphatic vessel candidates, and may further be determined as lymphatic vessels depending on an additional condition. The "lymphatic vessel determination range" can be set to a proper range as a range substantially excluding blood vessels and tissue surrounding lymphatic vessels by experiments, analysis, or the like. The calculated lymphatic vessels and blood vessels may be displayed on a display unit in such a manner that the lymphatic vessels and the blood vessels are distinguished from each other, such as in different colors or different patterns from each other. Both of the lymphatic vessels and the blood vessels may be displayed, and the display may be switched to either of the lymphatic vessels and the blood vessels as appropriate. Alternatively, the lymphatic vessels may be displayed instead of the blood vessels, and the device of the present embodiment may function as a "lymphatic vessel visualizing device".

Such a blood vessel extracting method may be applied to the process of computing a network of blood vessels in addition to the body motion noise removing method described above. Specifically, the OCT intensities of blood vessel candidates obtained after the body motion noise removal described above may be calculated as "actual intensity values". An average of intensity values in the remaining tomographic images may be used as an "actual intensity value". Blood vessel candidates having intensity values within the blood vessel determination range may be determined to be blood vessels. Such an additional process of the blood vessel extracting method may be performed only on dermis corresponding regions.

In addition, a blood vessel visualization program using the above-described technology may be built. The program causes a computer to implement a function of setting a reference profile obtained by function approximation of an intensity profile in the depth direction of a tomographic image acquired by the OCT, a function of calculating a difference between an intensity value on the reference profile and an actual intensity value as an outlier regarding the intensity value in the depth direction of the tomographic image, determining coordinates having the outliers within the preset blood vessel determination range to be blood vessels or blood vessel candidates, and calculating a network of blood vessels, and a function of outputting signals to display the calculated network of blood vessels. The program may be recorded on a computer-readable recording medium.

(3) Visualization of Blood Vessel Thickness

In general, supply of nutrients and excretion of wastes are smoother and skin is considered to be healthier as the capillaries in the skin are thicker. Thus, evaluation of skin can be more appropriately achieved if the thicknesses of blood vessels are visualized more properly in addition to visual display of a network of blood vessels as described above. Thus, in the present embodiment, the thicknesses of blood vessels are visually displayed as one of parameters of a network of blood vessels.

As described above, the control computation unit determines coordinates with the autocorrelation values of a plurality of acquired tomographic images of a skin site being within the preset low correlation range to be blood vessels, to calculate a network of blood vessels. Alternatively, the control computation unit may determine coordinates with OCT intensities equal to or smaller than a blood vessel determination reference value (or preferably coordinates within the blood vessel determination range) to be blood vessels, and calculate a network of blood vessels. In the present embodiment, a radius from each set of blood vessel corresponding coordinates determined as corresponding to a blood vessel and within which other sets of blood vessel corresponding coordinates are present is defined as a blood vessel radius. The "blood vessel radius" may be on the assumption of a virtual circle having its center at blood vessel corresponding coordinates. Alternatively, a center of a polygon close to a circle or other shapes may be set, and the blood vessel radius may be defined using the diameter of the polygon or the like (approximation to the radius). The control computation unit expresses the thicknesses of a network of blood vessels by superimposing distinctions based on the blood vessel radii from the respective sets of blood vessel corresponding coordinates onto the image of the network of blood vessels.

The control computation unit may gradually increase a radius from each set of blood vessel corresponding coordinates. When the radius has reached a value at which the proportion of surrounding blood vessel coordinates becomes lower than a preset proportion determination reference value, the control computation unit may determine, as the blood vessel radius, this value or a value immediately before the proportion becomes lower than the preset proportion determination reference value. Alternatively, in view of an error range, the control computation unit may determine, as the blood vessel radius, a value of the radius before or after the proportion becomes lower than the preset proportion determination reference value. The "proportion determination reference value" may be appropriately set depending on the resolution of the images, such as 98% or higher, or more preferably 99% or higher, which is substantially 100% (including the error range). The control computation unit may alternatively determine, as the "blood vessel radius", a value of the radius when or immediately before the proportion starts to decrease such as from 100% to 99%.

Specifically, the control computation unit may express the thicknesses of a network of blood vessels by using different colors at respective sets of blood vessel corresponding coordinates depending on the magnitudes of the blood vessel radii. The distinctions based on the magnitudes of the blood vessel radii are made in a superimposing manner as described above, which makes the thicknesses of blood vessels clear at a glance, as will also be presented in an example described later. In particular, this improves the visibility of blood vessel shapes at parts having complicated shapes such as diverging points and converging points of blood vessels.

In addition, a blood vessel visualization program using the above-described technology may be built. The program causes a computer to implement a function computing a network of blood vessels of skin on the basis of a tomographic image acquired by the OCT, and a function of determining, as a blood vessel radius, a radius from each set of blood vessel corresponding coordinates determined as corresponding to a blood vessel in the calculation of the network of blood vessels and within which other sets of blood vessel corresponding coordinates are present, and outputting signals to make distinctions based on the magnitudes of the blood vessel radii from the respective sets of blood vessel corresponding coordinates in a superimposing manner with display of the network of blood vessels. The program may be recorded on a computer-readable recording medium.

An example according to the present embodiment will now be described in detail with reference to the drawings.

EXAMPLE

FIG. 1 is a diagram schematically illustrating a configuration of a blood vessel visualizing device according to the example. The blood vessel visualizing device tomographically measures skin tissue in microscale, and visualizes the capillaries in the skin. The OCT is used for the tomographic measurement.

As illustrated in FIG. 1, an OCT device 1 includes a light source 2, an object arm 4, a reference arm 6, optical mechanisms 8 and 10, an optical detection device 12, a control computation unit 14, and a display device 16. The respective optical components are connected with each other by optical fibers. While an optical system based on a Mach-Zehnder interferometer is presented in FIG. 1, other optical systems such as a Michelson interferometer may alternatively be used.

While swept source OCT (SS-OCT) is used in this example, other types of OCT such as time domain OCT (TD-OCT) or spectral domain OCT (SD-OCT) may be used instead. The SS-OCT enables acquisition of data with high measurement sensitivity by using a light source with temporally swept emission wavelength without mechanical sweeping along the reference optical path, which is preferable in that high temporal resolution and high position detecting accuracy are achieved.

Light emitted from the light source 2 is split by a coupler 18 (beam splitter). One beam from the coupler 18 is guided to the object arm 4 and becomes object light, and the other is guided to the reference arm 6 and becomes reference light. The object light in the object arm 4 is guided to the optical mechanism 8 via a circulator 20, and directed to an object to be measured (hereinafter referred to as an "object S"). The object S is skin in this example. The object light is reflected as backscattered light at the surface and a cross section of the object S, returned to the circulator 20, and then guided to a coupler 22.

Meanwhile, the reference light at the reference arm 6 is guided to the optical mechanism 10 via a circulator 24. The reference light is reflected by a reference mirror 26 of the optical mechanism 10, returned to the circulator 24, and then guided to the coupler 22. Thus, the object light and the reference light are combined (superimposed) by the coupler 22, and interference light of the object light and the reference light is detected by the optical detection device 12. The optical detection device 12 detects the interference light as an optical interference signal (a signal indicating interference light intensity). The optical interference signal is input to the control computation unit 14 via an AD converter 28.

The control computation unit 14 performs control of the entire optical system, and arithmetic processing for outputting images using the OCT. Command signals from the control computation unit 14 are input to the light source 2, the optical mechanisms 8 and 10, and the like via a DA converter, which is not illustrated. The control computation unit 14 processes the optical interference signal input to the optical detection device 12, and acquires a tomographic image of the object S using the OCT. The control computation unit 14 then computes tomographic distribution of a network of blood vessels in the object S on the basis of the tomographic image data by a technique described later.

This will be described in more detail below.

The light source 2 is a wavelength swept light source that emits light with temporally swept emission wavelengths. Light emitted from the light source 2 is split by the coupler 18 into the object light and the reference light, which are guided to the object arm 4 and the reference arm 6, respectively.

The optical mechanism 8 is included in the object arm 4, and includes a mechanism for guiding light from the light source 2 to the object S to scan the object S, and a drive unit for driving the mechanism. The optical mechanism 8 includes a collimator lens 30, a two-axis galvanometer mirror 32, and an object lens 34. The object lens 34 is arranged to face the object S. Light having passed through the circulator 20 is guided to the galvanometer mirror 32 via the collimator lens 30, scanned in the x-axis direction and the y-axis direction, and directed to the object S. Light reflected by the object S is returned as object light to the circulator 20, and guided to the coupler 22.

The optical mechanism 10 is included in the reference arm 6, and includes a collimator lens 40, a focusing lens 27, and the reference mirror 26. Light having passed through the circulator 24 is focused on the reference mirror 26 by the focusing lens 27 via the collimator lens 40. This reference light is reflected by the reference mirror 26, thus returned to the circulator 24, and guided to the coupler 22. The reference light is then superimposed with the object light, and sent as interference light to the optical detection device 12.

The optical detection device 12 includes a photodetector 42 and an amplifier 44. The interference light obtained through the coupler 22 is detected as an optical interference signal by the photodetector 42. The optical interference signal is input to the control computation unit 14 via the amplifier 44 and the AD converter 28.

The control computation unit 14 includes a CPU, a ROM, a RAM, a hard disk, and the like. The control computation unit 14 performs, by the hardware and software, control of the entire optical system, and arithmetic processing for outputting images by the OCT. The control computation unit 14 controls driving of the optical mechanisms 8 and 10, processes the optical interference signal output from the optical detection device 12 on the basis of the driving, and acquires tomographic images of the object S obtained by the OCT. The control computation unit 14 then computes a network of blood vessels in the object S by a technique that will be described later on the basis of the tomographic image data.

The display device 16 is constituted by a liquid crystal display, for example, and functions as a "display unit". The display device 16 displays the network of blood vessels in the object S computed by the control computation unit 14 in two-dimensional or three-dimensional visualization.

A method of arithmetic processing for calculating a network of blood vessels in skin will now be explained.

As described above, according to the OCT, the object light (reflected light from the object S) having passed through the object arm 4 and the reference light having passed through the reference arm 6 are combined, and detected as an optical interference signal by the optical detection device 12. The control computation unit 14 is capable of acquiring the optical interference signal as a tomographic image of the object S based on the interference light intensity (OCT intensity).

A coherence length $l_c$, which represents the resolution in the optical axis direction (depth direction) of the OCT is determined by an autocorrelation function of the light source. Herein, the coherence length $l_c$ is the half width at half maximum of the envelope of the autocorrelation function, and can be expressed by the following expression (1).

$$l_c = \frac{2 \ln 2}{\pi} \left( \frac{\lambda_c^2}{\Delta \lambda} \right) \qquad (1)$$

In the expression (1), $\lambda_c$ represents the center wavelength of a beam, and $\Delta\lambda$ represents the full width at half maximum of the beam.

In addition, the resolution in the direction perpendicular to the optical axis (beam scanning direction) is ½ of a beam-spot diameter D on the basis of the focusing performance of a focusing lens. The beam-spot diameter $\Delta\Omega$ can be expressed by the following expression (2).

$$\Delta\Omega = \frac{4\lambda_c}{\pi} \left( \frac{f}{d} \right) \qquad (2)$$

In the expression (2), d represents the diameter of a beam incident on the focusing lens, and f represents the focal point of the focusing lens.

Figure 2A:
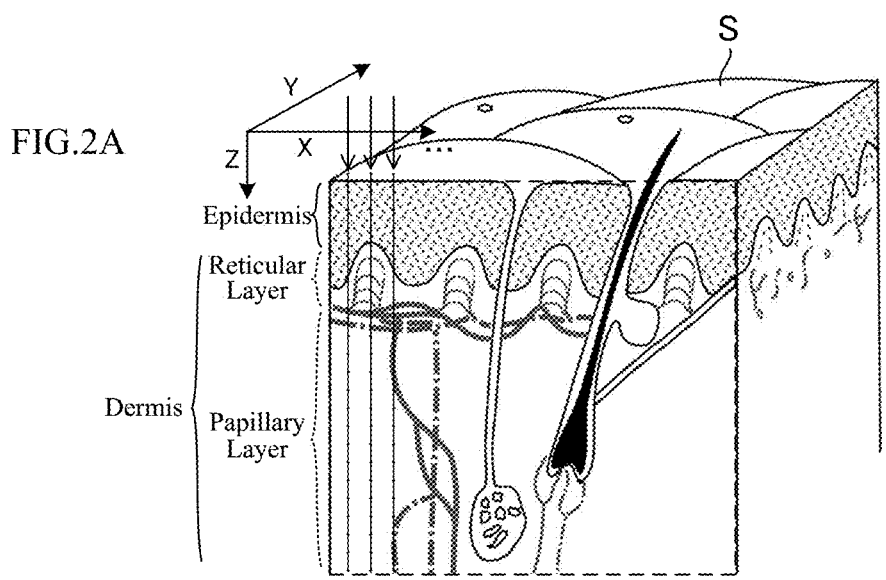
FIGS. 2A to 2C are explanatory views showing a basic method for detecting a network of blood vessels.
Figure 2B:
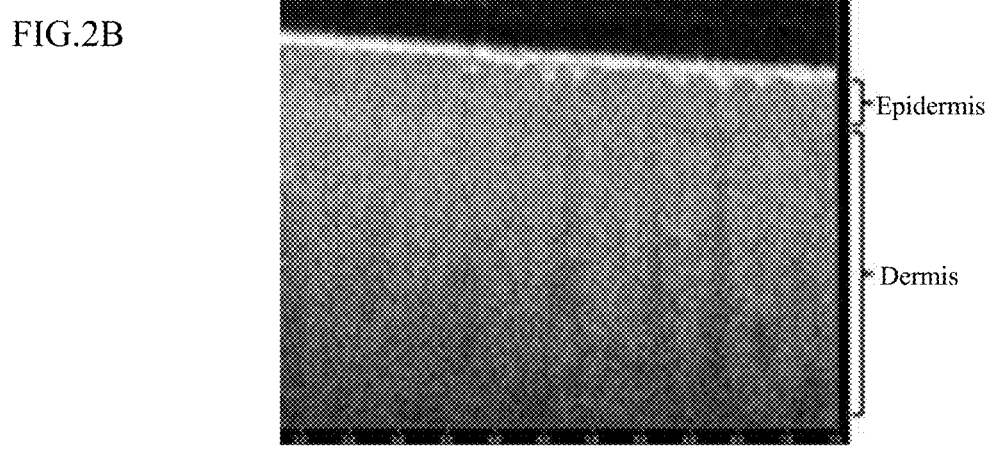
Figure 2C:
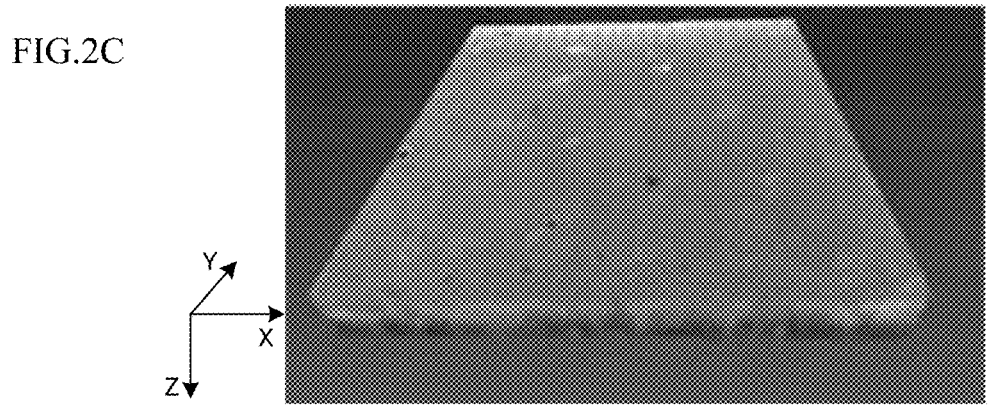

A network of blood vessels (shapes of blood vessels and changes thereof) can be calculated through computation of autocorrelation of a plurality of tomographic images of each site acquired by the OCT. FIGS. 2A to 2C are explanatory views showing a basic method for detecting a network of blood vessels. FIG. 2A shows a method of measuring skin (an object S) by the OCT. FIG. 2B illustrates a two-dimensional tomographic image, and FIG. 2C illustrates a three-dimensional tomographic image.

As illustrated in FIG. 2A, capillaries run in and under dermis of skin. In FIG. 2A, arteries are illustrated by solid lines, and veins are illustrated by alternate long and short dashed lines. No blood vessels are present in epidermis. Portions projecting toward the epidermis in upper part of the dermis correspond to a papillary layer, which includes very thin blood vessels. A reticular layer is present under the papillary layer. Relatively thick blood vessels are present in the reticular layer.

In OCT measurement, the optical axis direction of the object light is set to the depth direction of the skin, and referred to as a Z direction. An X direction and a Y direction are set to directions perpendicular to the Z direction. First, a two-dimensional measurement region is set on a Z-X plane (see a frame in broken line), and Z-direction scanning using wavelength sweeping according to the SS-OCT is performed. The Z-direction scanning is repeated while being shifted in the X direction. As a result, a two-dimensional tomographic image as shown in FIG. 2B is obtained. Y-direction scanning is further performed, and a three-dimensional tomographic image as shown in FIG. 2C is thus obtained. Because such OCT measurement has high resolution in microscale, even noise caused by body motion of a subject (body motion noise) is not negligible in some cases.

Figure 3A:
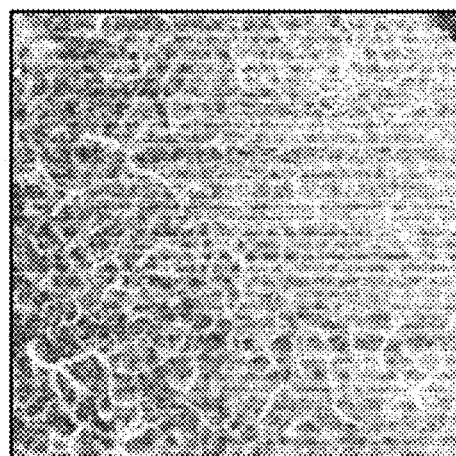
FIGS. 3A to 3D are explanatory views showing the influence of noise in detection of a network of blood vessels by the OCT.
Figure 3B:
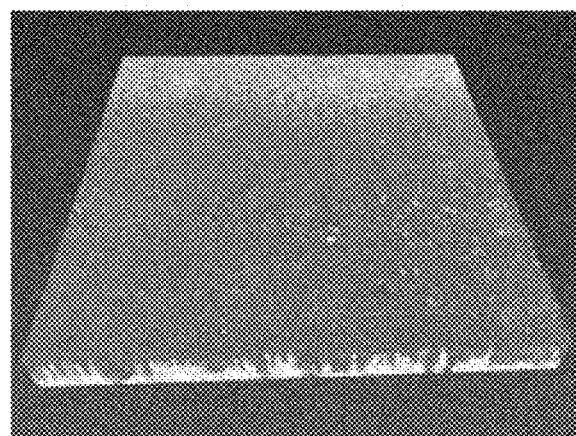
Figure 3C:
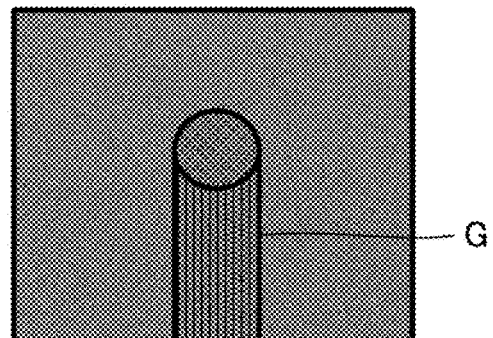
Figure 3D:
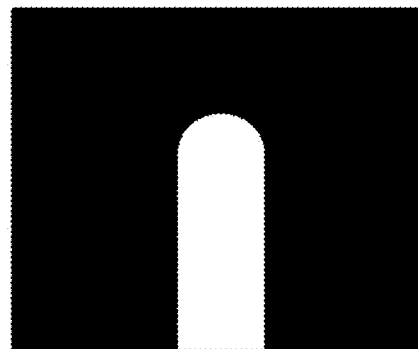

FIGS. 3A to 3D are explanatory views showing the influence of noise in detection of a network of blood vessels by the OCT. FIG. 3A shows the influence of body motion noise. FIGS. 3B to 3D show the influence of noise due to blood flows. In FIG. 3A, high-intensity portions (white portions) represent a network of blood vessels at a predetermined cross-section (X-Y cross-section). It can be seen that body motion noise is superimposed on the network of blood vessels, which makes the entire image blurred in white.

In addition, as shown in FIG. 3B, in three-dimensional display, it can be seen that lower part of a Z-X cross section is blurred in white. This is considered to be because blood flows in the reticular layer of the dermis have increased, resulting in that a detected image has been shaken in the Z direction, which has caused a so-called "motion ghost G"

shown in FIG. 3C. When the motion ghost G occurs, calculated blood vessel likelihood data extends in the Z direction as shown in FIG. 3D, which does not correspond to the actual blood vessels. Noise caused by the motion ghost will also be referred to as "blood flow noise". In this example, a body motion noise removing process and a blood vessel extracting process are performed to solve such problems.

Body Motion Noise Removing Process

In calculation of a network of blood vessels, an interrogation region (inspection region) (a region of 3×3 pixels, for example) is set in each of continuously acquired tomographic images of a skin site, and autocorrelation within the interrogation regions is computed. Specifically, the identity (similarity) of images at the sane coordinates in the interrogation regions is calculated as an autocorrelation value. As the autocorrelation is higher, it is determined that less displacement (deformation) is present in the images, that is, the motion of skin tissue at the coordinates is smaller. Conversely, as the autocorrelation is lower, it is determined that the motion of skin tissue at the coordinates is larger. Because blood vessels vary depending on blood flows, blood vessels have lower autocorrelation than surrounding tissue. On the basis of this feature, coordinates (pixel) at which autocorrelation is low can be determined as having high blood vessel likelihood, that is, as a blood vessel or a blood vessel candidate.

When body motion noise is present, however, tissue also varies (deforms), and has low autocorrelation. Thus, when the autocorrelation is low, it is preferable that it can be determined whether the low autocorrelation is due to blood flows or body motion noise, and that the latter can be removed. Focus is therefore placed on a structural difference in that no blood vessels are present in epidermis while blood vessels are present in dermis. Because the epidermis does not include blood vessels, the autocorrelation in the epidermis should normally be high. When the autocorrelation is nonetheless significantly low in the epidermis, it can be likely to be due to the influence of body motion noise.

Typically, in obtaining autocorrelation in a plurality of tomographic images acquired for calculation of a network of blood vessels, autocorrelation values are calculated for all combinations of the tomographic images, and the autocorrelation is evaluated on the basis of an average of the calculated autocorrelation values. In this example, combinations of topographic images in which the autocorrelation in the epidermis is low are excluded in advance, so that contamination of body motion noise is prevented or reduced. Autocorrelation is then obtained from the remaining combinations of the tomographic images, and a network of blood vessels with reduced body motion noise is calculated.

Specifically, the following arithmetic processing is performed.

When a tomographic image of one cross section is acquired T times by the OCT, the OCT intensity (light intensity) at coordinates (p,q) in a t-th tomographic image are represented by $I_t(p,q)$, and an average of the OCT intensities within an interrogation region with its center at the coordinates (p,q) is represented by $\overline{I_t}(p,q)$. In this case, an autocorrelation value $P_{epi}^{t1,t2}(p,q)$ obtained by normalization at the coordinates (p,q) in an epidermis corresponding regions in t1-th and t2-th (t1≠t2) tomographic images is expressed by the following expression (3).

$$P_{epi}^{t1,t2}(p,q) = \frac{\Sigma_q \Sigma_p (I_{t1}(p,q) - \overline{I_{t1}})(I_{t2}(p,q) - \overline{I_{t2}})}{\sqrt{\Sigma_q \Sigma_p (I_{t1}(p,q) - \overline{I_{t1}})^2 \times \Sigma_q \Sigma_p (I_{t2}(p,q) - \overline{I_{t2}})^2}} \quad (3)$$

The control computation unit 14 obtains a set $PS_{epi}$, which is rearrangement in descending order of a set $P_{epi}$ of such autocorrelation values $P_{epi}^{t1,t2}(p,q)$ (a set of autocorrelation data), by the following expression (4).

$$P_{epi} \ni \{P_{epi}^{1,2}, P_{epi}^{1,3}, \ldots, P_{epi}^{T-1,T}\}$$

$$PS_{epi} = \text{sort}\{P_{epi}, ASC\} \quad (4)$$

The control computation unit 14 then deletes (M+1)-th and subsequent data in the set $PS_{epi}$, M being a predetermined number. That is, data with which predetermined low autocorrelation is obtained in an epidermis corresponding region are determined as being affected by body motion noise and excluded. In other words, combinations of tomographic images having low autocorrelation in an epidermis corresponding region are excluded. The remaining data, that is, the first to M-th data with high autocorrelation in the epidermis corresponding region are used for determination of a network of blood vessels.

Specifically, a normalized autocorrelation value $P_{derm}^{t1,t2}(p,q)$ in a dermis corresponding region is calculated for the remaining combinations of tomographic images by the following expression (5).

$$P_{derm}^{t1,t2}(p,q) = \frac{\Sigma_q \Sigma_p (I_{t1}(p,q) - \overline{I_{t1}})(I_{t2}(p,q) - \overline{I_{t2}})}{\sqrt{\Sigma_q \Sigma_p (I_{t1}(p,q) - \overline{I_{t1}})^2 \times \Sigma_q \Sigma_p (I_{t2}(p,q) - \overline{I_{t2}})^2}} \quad (5)$$

The combinations of t1 and t2 are those that are not deleted in the aforementioned expression (4).

The control computation unit 14 then determines coordinates at which the autocorrelation value $P_{derm}^{t1,t2}(p,q)$ is in a predetermined low correlation range to be blood vessel candidates.

Blood Vessel Extracting Process

Some of the blood vessel candidates obtained as described above may include lymphatic vessels. In addition, a motion ghost may be present at a portion of a large blood flow. To solve such problems, a process for selecting blood vessels from blood vessel candidates is performed.

Figure 4:
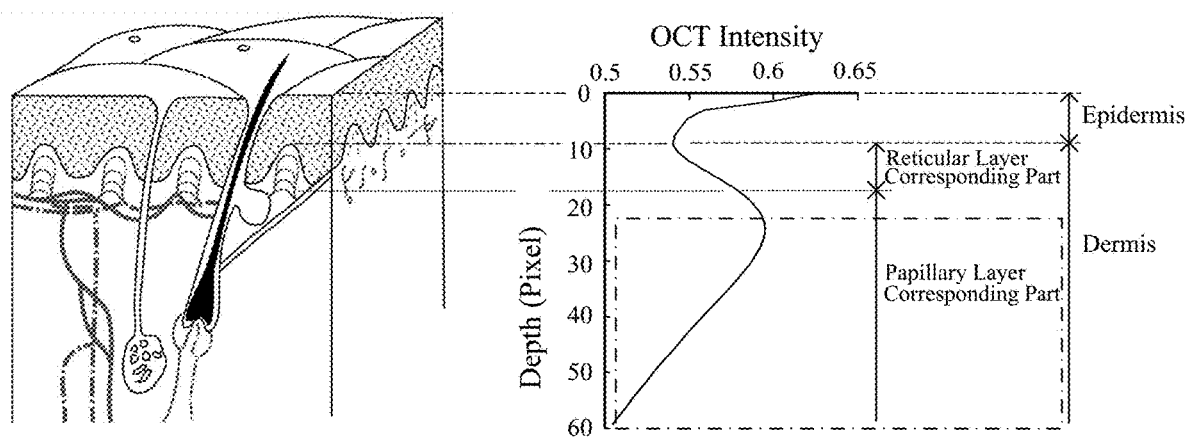
FIG. 4 is an explanatory diagram schematically illustrating a blood vessel extracting method.
Figure 5A:
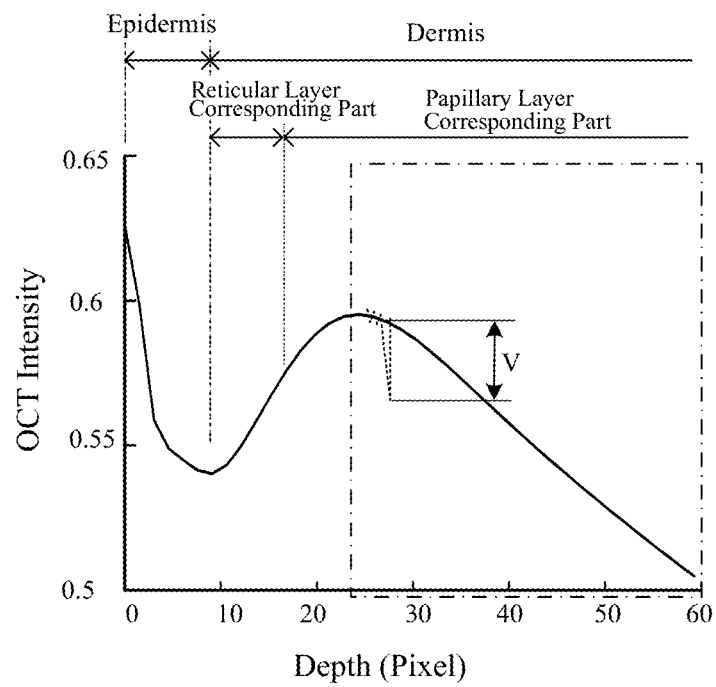
FIGS. 5A and 5B are explanatory diagrams schematically illustrating the blood vessel extracting method.
Figure 5B:
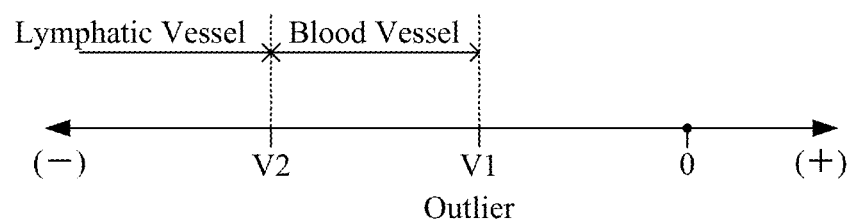

FIG. 4, FIGS. 5A and 5B are explanatory diagrams schematically illustrating a blood vessel extracting method.

In this example, as illustrated in the right part of FIG. 4, an intensity profile showing the relation between the depth from a skin surface and OCT intensity is obtained on the basis of the acquired tomographic images. Herein, the depth is expressed by a pixel value in the Z direction. The OCT intensity may be an average of data in a plurality of tomographic images of a skin site. A position with the highest OCT intensity (depth=0) corresponds to the skin surface. The intensity profile is a curve including a minimum value and a maximum value as illustrated. A range from the skin surface to approximately the minimum value is considered as corresponding to the epidermis. In addition, according to a literature (Neerken, S., Characterization of age-related effects in human skin, J Biomed Opt, 9 (2004) 274-281.), the boundary between a papillary layer corresponding part and a reticular layer corresponding part in the dermis is considered as being present between the minimum value and the maximum value.

Note that a portion of a large blood flow at which a motion ghost may occur is considered to correspond to a reticular layer corresponding part in which blood vessels are relatively thick. Thus, blood vessel candidates having high blood vessel likelihood in the reticular layer corresponding part are extracted.

FIG. 5A shows a reference profile, and FIG. 5B shows a blood vessel determination range.

The control computation unit 14 holds the reference profile obtained by function approximation of the intensity profile illustrated in the right part of FIG. 4 (FIG. 5A). More specifically, the reference profile is obtained by linear fitting of the intensity profile at a depth deeper than the position at which the OCT intensity is maximum in the reticular layer corresponding part (see a frame in alternate long and short dashed line). Such function approximation makes the OCT intensity on the reference profile closer to the intensity of skin tissue surrounding blood vessels and lymphatic vessels. In other words, when the OCT intensity at a position deviates significantly from the reference profile, the position is considered as corresponding to a blood vessel or a lymphatic vessel.

Thus, in this example, as illustrated in FIG. 5B, a difference between the intensity value on the reference profile and the actual intensity value at the same depth is defined as an outlier (outlier level). While an "outlier V" is defined as a value obtained by subtracting the intensity value on the reference profile from the actual intensity value and is thus a negative value in the example illustrated in FIG. 5B, the outlier V may be defined as a value obtained by the reverse of the subtraction. A range in which the outlier V is V1 to V2 is the "blood vessel determination range", and a range in which the outlier is larger than V2 is the "lymphatic vessel determination range".

Coordinates (pixel) having the outlier within the blood vessel determination range in an OCT image can be determined to correspond to a blood vessel or a blood vessel candidate. Among blood vessel candidates in the reticular layer corresponding part obtained through the body motion noise removing process, the control computation unit 14 determines a blood vessel candidate having the outlier within the blood vessel determination range to be a blood vessel.

Figure 6A:
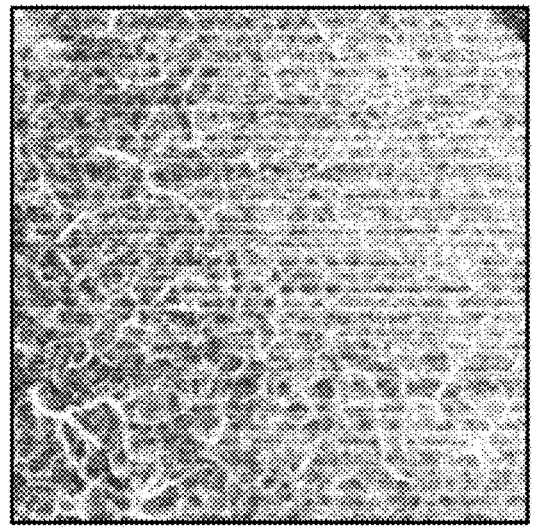
FIGS. 6A and 6B show results of calculation of a network of blood vessels.
Figure 6B:
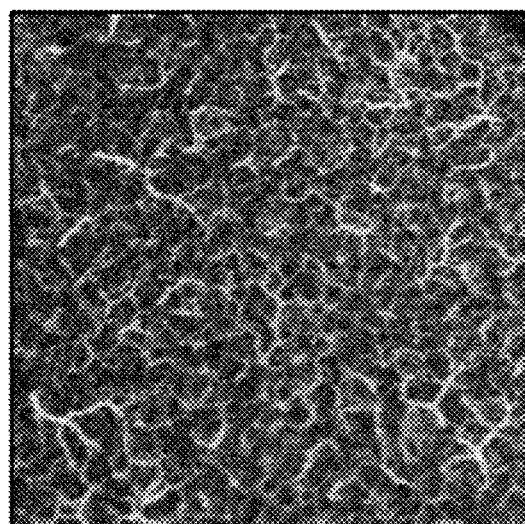

FIGS. 6A, 6B, 7A to 7D show results of calculation of a network of blood vessels. FIG. 6A shows a case where the body motion noise removing process has not been performed, and FIG. 6B shows a case where the body motion noise removing process has been performed. FIGS. 7A to 7D show a plurality of images (images of X-Y cross sections) at different depths from the skin surface. The depths are 63 μm, 108 μm, 323 μm, and 431 μm, respectively. In each of FIGS. 7A to 7D, the upper part shows an OCT image, and the lower part shows a result of calculation of a network of blood vessels.

In FIGS. 6A and 6B, it can be seen that the body motion noise removing process as in this example clearly reduces noise and increases the visibility. In addition, in FIGS. 7A to 7D, it can be seen that a network of blood vessels is thicker as the depth under the skin is larger, and thus the obtained image is close to the actual blood vessels.

Blood Vessel Parameter Displaying Process

Figure 8A:
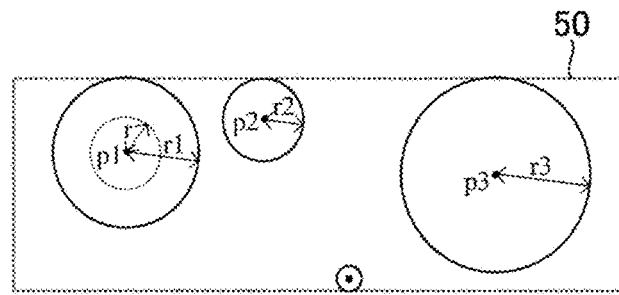
Figure 8A:
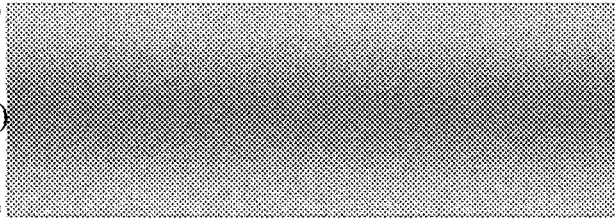
Figure 8C:
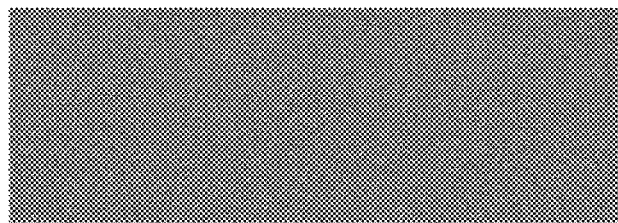

In this example, information on the thicknesses of blood vessels is visually displayed in a superimposing manner on the network of blood vessels obtained as described above. FIGS. 8A to 8C illustrate process stages of a blood vessel thickness displaying process.

The control computation unit 14 calculates a blood vessel radius from each set of coordinates (blood vessel corresponding coordinates) determined to correspond to a blood vessel as described above. As schematically illustrated in FIG. 8A, a radius from blood vessel corresponding coordinates included in a network of blood vessels 50 and within which other sets of blood vessel corresponding coordinates are present is defined as a blood vessel radius r. Specifically, a radius of a circle with its center at the set of blood vessel corresponding coordinates is gradually increased, and the value of the radius when the ratio of the area of the blood vessel corresponding coordinates to the area of the circle starts to decrease is determined as the blood vessel radius r. Conceptually, the value of the radius of the circle with its center at the set of blood vessel corresponding coordinates when the circle reaches the blood vessel wall corresponds to the blood vessel radius r. In the example illustrated in FIG. 8A, r1 is obtained as the blood vessel radius at coordinates p1, r2 is obtained as the blood vessel radius at coordinates p2, and r3 is obtained as the blood vessel radius at coordinates p3.

In addition, as illustrated in FIG. 8B, the control computation unit 14 uses different colors at respective sets of blood vessel corresponding coordinates depending on the magnitudes of the blood vessel radii. The blood vessel radius is smaller as the set of blood vessel corresponding coordinates is closer to the blood vessel. To correct this, as illustrated in FIG. 8C, the control computation unit 14 subsequently applies a circular Kernel maximum filter, which is a filter for filling a circular region with a value of a center of the maximum circle within the region, to color the respective sets of blood corresponding coordinates with different colors depending on the blood vessel radii. Although the blood vessel radii are equal and the blood vessel corresponding coordinates are filled with the same color in the example illustrated in FIG 8C, a color change will be displayed at blood vessel corresponding coordinates where the blood vessel radius changes.

Figure 9A:
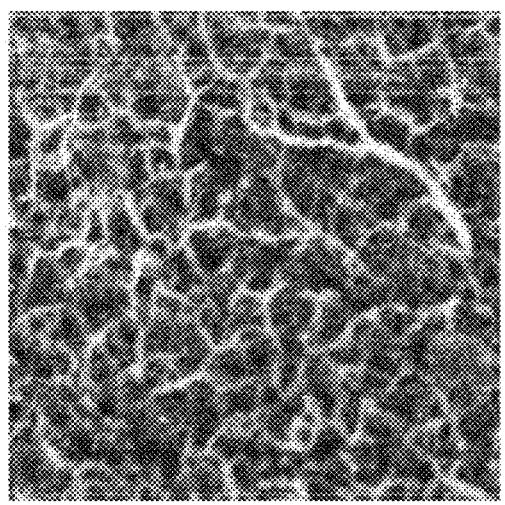
FIGS. 9A to 9C show results of visualization of blood vessel thicknesses.
Figure 9B:
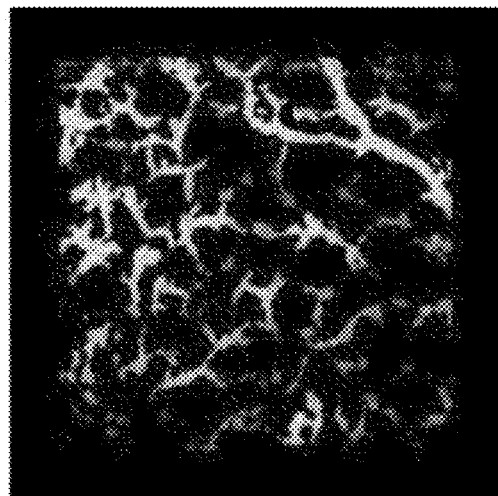
Figure 9C:
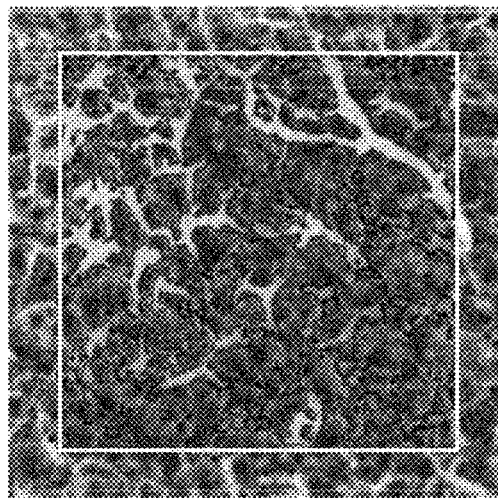
Figure 10A:
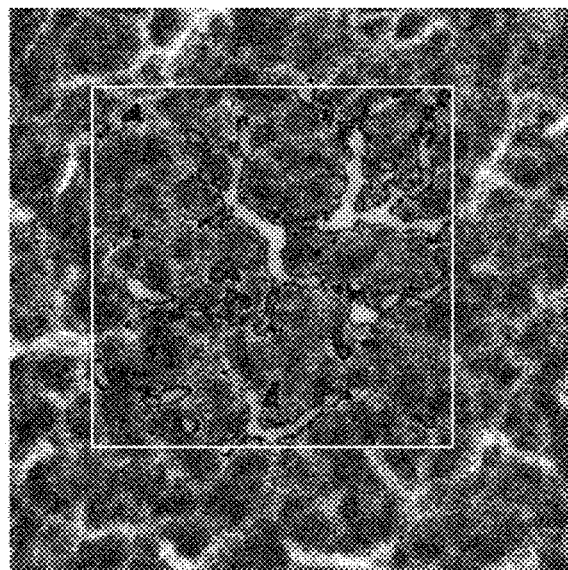
FIGS. 10A and 10B show states of epidermis when thermal load is applied.
Figure 10A:
Figure 10B:
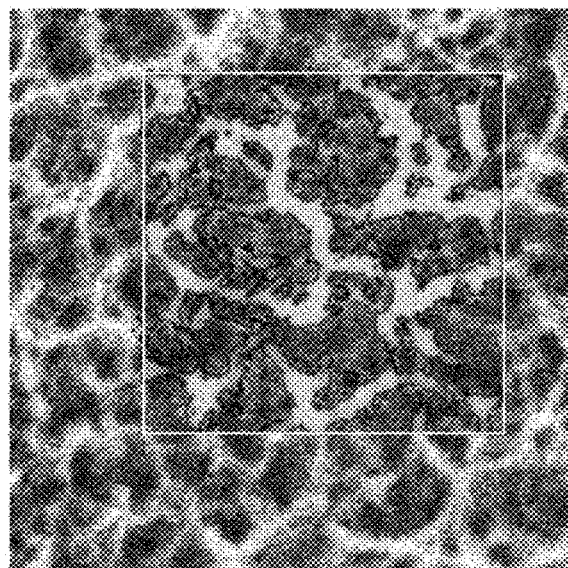
Figure 10B:

FIGS. 9A to 9C show results of visualization of blood vessel thicknesses. Specifically, FIGS. 9A to 9C show processes of display of the blood vessel thicknesses. FIGS. 10A and 10B show states of the epidermis when thermal load is applied. FIG. 10A shows a state before thermal load is applied, and FIG. 10B shows a state after thermal load is applied.

The control computation unit 14 displays an image of a network of blood vessels shown in FIG. 9A, and computes a thickness distinguishing image shown in FIG. 9B. In addition, the control computation unit 14 superimposes the thickness distinguishing image on the blood vessel network image as shown in FIG. 9C to express the thicknesses of the network of blood vessels.

As shown in FIGS. 10A and 10B, the thickness distinguishing image changes before and after application of thermal load. It can be seen that the thicknesses are increased after the application of thermal load. Thus, a result that matches the actual state in which blood vessels expand owing to thermal load is obtained.

Next, a flow of specific processes performed by the control computation unit 14 will be explained.

Figure 11:
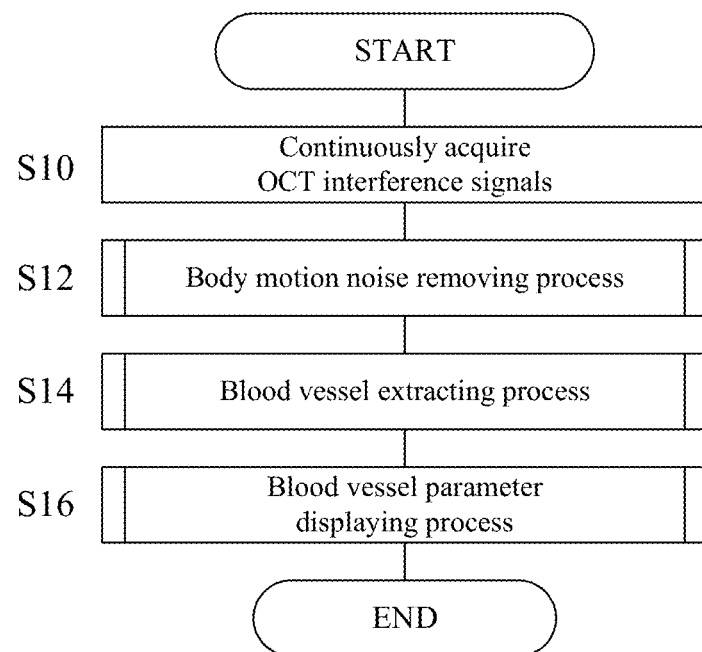
FIG. 11 is a flowchart illustrating a flow of a blood vessel network visualizing process.

FIG. 11 is a flowchart illustrating a flow of a blood vessel network visualizing process performed by the control computation unit 14. This process is repeated for a predetermined computation period. The control computation unit 14 acquires a plurality of optical interference signals by the OCT while controlling driving of the light source 2 and the optical mechanisms 8 and 10 (S10). The control computation unit 14 sequentially performs the body motion noise removing process (S12), the blood vessel extracting process (S14), and the blood vessel parameter displaying process (S16) described above on the acquired OCT images.

Figure 12:
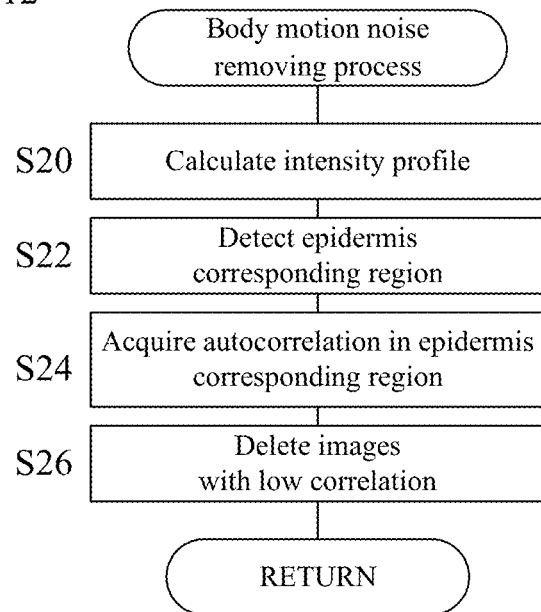
FIG. 12 is a flowchart illustrating a body motion noise removing process in detail.

FIG. 12 is a flowchart illustrating the body motion noise removing process in S12 of FIG. 11 in detail. The control computation unit 14 calculates the intensity profile described above on the basis of the acquired OCT images (S20), and detect an epidermis corresponding region (S22). The control computation unit 14 then performs an autocorrelation process on the epidermis corresponding region (S24), and deletes images with low correlation to remove body motion noise (S26).

Figure 13:
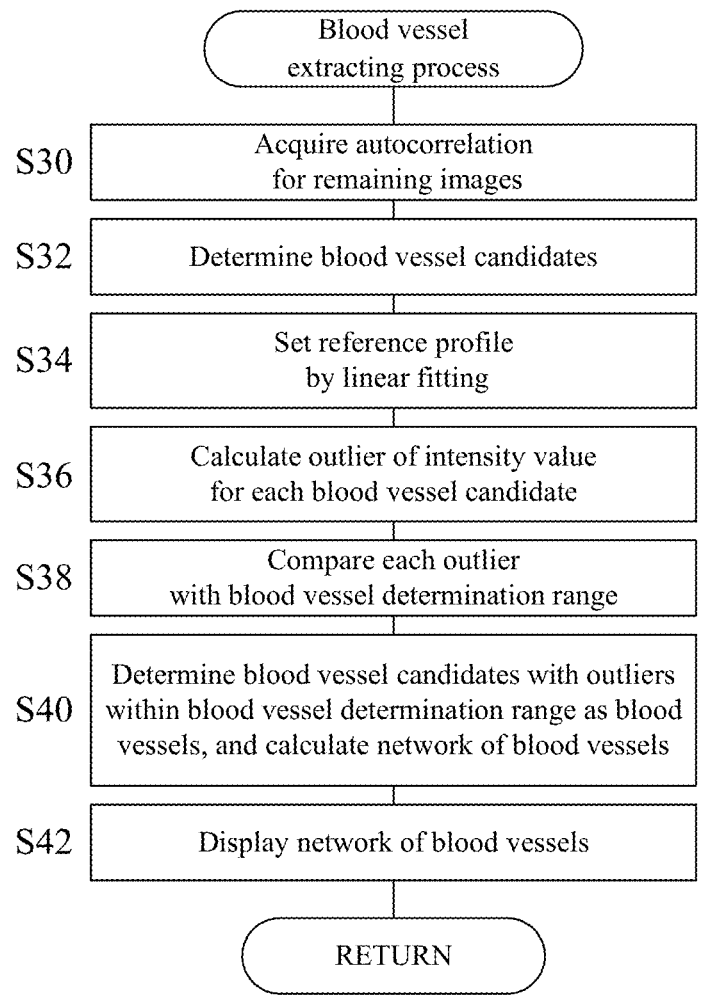
FIG. 13 is a flowchart illustrating a blood vessel extracting process in detail.

FIG. 13 is a flowchart illustrating the blood vessel extracting process in S14 of FIG. 11 in detail.

The control computation unit 14 acquires an autocorrelation value for the remaining tomographic images that have not been removed in S26 (S30), and determines coordinates present in the low correlation range as blood vessel candidates (S32).

In addition, the control computation unit 14 performs linear fitting on the intensity profile, and sets a reference profile for a reticular layer corresponding region (S34). The control computation unit 14 then calculates an outlier of an intensity value (OCT intensity) for each of coordinates determined to be blood vessel candidates in S32 (S36), and compares each of the outliers with the blood vessel determination range (S38). Subsequently, the control computation unit 14 determines blood vessel candidates with the outliers being within the blood vessel determination range as blood vessels, and calculates a network of blood vessels that is a set of the blood vessels (S40). The control computation unit 14 then displays the thus obtained network of blood vessels on the display device 16 (S42).

Figure 14:
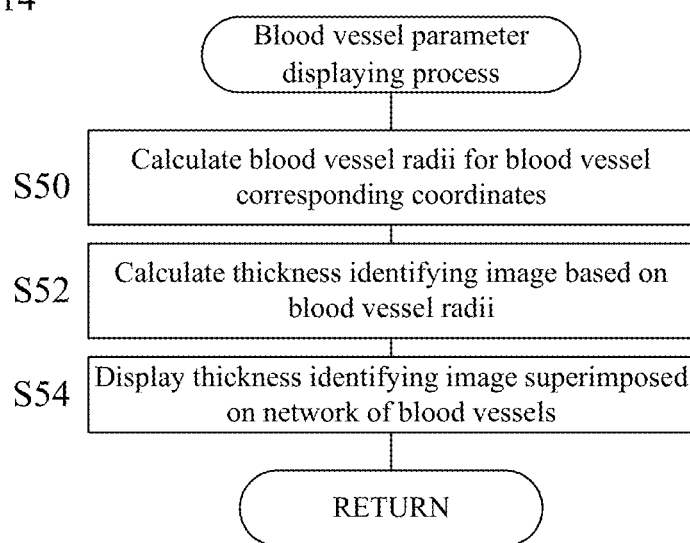
FIG. 14 is a flowchart illustrating a blood vessel parameter displaying process in detail.

FIG. 14 is a flowchart illustrating the blood vessel parameter displaying process in S16 of FIG. 11 in detail. The control computation unit 14 calculates blood vessel radii from blood vessel corresponding coordinates of the blood vessels obtained in S40 (S50), and computes a thickness distinguishing image on the basis of the blood vessel radii (S52). The control computation unit 14 then displays the thickness distinguishing image superimposed on the blood vessel network image of S42 (S54).

The description of the present invention given above is based on illustrative examples. It will be obvious to those skilled in the art that the present invention is not limited to the particular examples but various modifications could be further developed within the technical idea underlying the present invention.

In the above-described example, an example in which a plurality of two-dimensional tomographic images are acquired by the OCT (so-called B-scan) and body motion noise is removed in units of B-scan on the basis of autocorrelation of the two-dimensional tomographic images has been presented. In a modification, autocorrelation may be obtained in units of Z-direction scanning (so-called A-scan), and body motion noise may be removed in units of A-scan.

While an example in which autocorrelation of tomographic images is computed using two-dimensional coordinates has been presented in the above-described example, the autocorrelation may be computed using three-dimensional coordinates.

In the above-described example, an example in which combinations of tomographic images with low autocorrelation in the epidermis corresponding region are removed for removal of body motion noise has been presented. In a modification, one tomographic image of such combination of tomographic images with which low autocorrelation is obtained may be deleted. The one tomographic image that is deleted is a tomographic image with which low autocorrelation is likely to be obtained. For example, a tomographic image that is shared by a plurality of combinations of tomographic images with which low autocorrelation is obtained may be deleted. In another modification, combinations of tomographic images with which low autocorrelation is obtained in all of the layers in a region to be analyzed including an epidermis corresponding region may be deleted.

While the process of FIG. 8C is performed after the process of FIG. 8B for visualization of blood vessel thicknesses in the above-described example, the process of FIG. 8C may be omitted. The process of FIG. 8C, however, makes distinctions of the blood vessel thicknesses clearer.

Although not mentioned in the above-described example, a noise reducing process using a spatial frequency filter, a median filter or the like may be performed to remove so-called line noise and salt-and-pepper noise after the body motion noise removing process or the blood vessel extracting process.

The present invention is not limited to the above-described examples and modifications only, and the components may be further modified to arrive at various other examples without departing from the scope of the invention. Various other examples may be further achieved by combining, as appropriate, a plurality of components disclosed in the above-described example and modifications. Furthermore, one or some of all of the components exemplified in the above-described example and modifications may be left unused or removed.

What is claimed is:

1. A blood vessel visualizing device that includes an optical system using optical coherence tomography, and visualizes a network of blood vessels of skin, the blood vessel visualizing device comprising:
    an optical mechanism that guides light from a light source to tissue of the skin to scan the skin tissue;
    a control computation unit that controls driving of the optical mechanism, acquires tomographic images of the skin by processing optical interference signals from the optical system, and calculates a network of blood vessels on the basis of the tomographic images; and
    a display unit that displays an image of the network of blood vessels, wherein
    the control computation unit computes autocorrelation values at coordinates in epidermis corresponding regions of a plurality of acquired tomographic images of each skin site,
    the control computation unit excludes combinations of tomographic images with the computed autocorrelation values corresponding to predetermined low autocorrelation, and then computes autocorrelation values at coordinates in dermis corresponding regions, and
    the control computation unit determines, as blood vessels or blood vessel candidates, coordinates at which the autocorrelation values in the dermis corresponding regions are within a predetermined low correlation range, and calculates the network of blood vessels.

2. The blood vessel visualizing device according to claim 1, wherein the control computation unit determines a region to be the epidermis corresponding region or the dermis corresponding region on the basis of an intensity profile in a depth direction in the acquired tomographic images.

3. The blood vessel visualizing device according to claim 2, wherein
the control computation unit determines, as blood vessel candidates, coordinates within the low correlation range,
the control computation unit holds a reference profile obtained by function approximation of an intensity profile in a depth direction in the acquired tomographic images,
the control computation unit calculates a difference between an intensity value on the reference profile and an actual intensity value as an outlier, the intensity values being those in a depth direction in the tomographic images, and determines, as a blood vessel candidate region, a region of coordinates with the outliers within a predetermined blood vessel determination range, and
the control computation unit determines blood vessel candidates within the blood vessel candidate region to be blood vessels.

4. The blood vessel visualizing device according to claim 2, wherein
the control computation unit obtains, as a blood vessel radius, a radius from a set of blood vessel corresponding coordinates determined to be a blood vessel and within which other sets of blood vessel corresponding coordinates are present, and
the control computation unit superimposes distinctions based on magnitudes of blood vessel radii from respective sets of blood vessel corresponding coordinates on an image of the network of blood vessels to express thicknesses of the network of blood vessels.

5. The blood vessel visualizing device according to claim 1, wherein
the control computation unit determines, as blood vessel candidates, coordinates within the low correlation range,
the control computation unit holds a reference profile obtained by function approximation of an intensity profile in a depth direction in the acquired tomographic images,
the control computation unit calculates a difference between an intensity value on the reference profile and an actual intensity value as an outlier, the intensity values being those in a depth direction in the tomographic images, and determines, as a blood vessel candidate region, a region of coordinates with the outliers within a predetermined blood vessel determination range, and
the control computation unit determines blood vessel candidates within the blood vessel candidate region to be blood vessels.

6. The blood vessel visualizing device according to claim 5, wherein
the control computation unit obtains, as a blood vessel radius, a radius from a set of blood vessel corresponding coordinates determined to be a blood vessel and within which other sets of blood vessel corresponding coordinates are present, and
the control computation unit superimposes distinctions based on magnitudes of blood vessel radii from respective sets of blood vessel corresponding coordinates on an image of the network of blood vessels to express thicknesses of the network of blood vessels.

7. The blood vessel visualizing device according to claim 1, wherein
the control computation unit obtains, as a blood vessel radius, a radius from a set of blood vessel corresponding coordinates determined to be a blood vessel and within which other sets of blood vessel corresponding coordinates are present, and
the control computation unit superimposes distinctions based on magnitudes of blood vessel radii from respective sets of blood vessel corresponding coordinates on an image of the network of blood vessels to express thicknesses of the network of blood vessels.

8. A blood vessel visualizing method for visualizing a network of blood vessels of skin, the method comprising:
a tomographic image acquiring step of acquiring a plurality of tomographic images of a skin site by using optical coherence tomography;
a first correlation acquiring step of acquiring autocorrelation in epidermis corresponding regions of the acquired tomographic images;
a second correlation acquiring step of excluding combinations of tomographic images with the acquired autocorrelation corresponding to predetermined low autocorrelation, and then acquiring autocorrelation in dermis corresponding regions;
a computing step of calculating a network of blood vessels on the basis of the autocorrelation in the dermis corresponding regions; and
a displaying step of displaying the calculated network of blood vessels.

9. A blood vessel visualizing method for visualizing a network of blood vessels of skin, the method comprising:
a tomographic image acquiring step of acquiring tomographic images of the skin by using optical coherence tomography;
a computation specifying step of determining tomographic images in which influence of noise due to body motion exceeds a reference value among the acquired tomographic images, and excluding the determined tomographic images from computation;
a computing step of calculating a network of blood vessels on the basis of tomographic images subject to computation; and
a displaying step of displaying the calculated network of blood vessels.

10. A non-transitory computer readable medium comprising a program for causing a computer to implement: a function of computing first autocorrelation values of a plurality of tomographic images of a skin site acquired by using optical coherence tomography, a first autocorrelation value being an autocorrelation value in epidermis corresponding regions; a function of excluding combinations of tomographic images with the first autocorrelation values corresponding to predetermined low autocorrelation, and then computing second autocorrelation values, the second autocorrelation values being autocorrelation values in dermis corresponding regions; a function of calculating a network of blood vessels on the basis of the second autocorrelation values; and a function of outputting signals to display the calculated network of blood vessels.

* * * * *